United States Patent [19]

Minami et al.

[11] Patent Number: 5,364,963

[45] Date of Patent: Nov. 15, 1994

[54] SUPPORTED RHODIUM CATALYST, METHOD OF PREPARING SAME AND PROCESS OF PRODUCING ACETIC ACID BY METHANOL CARBONYLATION USING SAME

[75] Inventors: Takeshi Minami; Kenji Shimokawa, both of Yokohama; Kazuhiko Hamato, Kawasaki; Yoshimi Shiroto, Yokohama; Noriyuki Yoneda, Tokyo, all of Japan

[73] Assignee: Chiyoda Corporation, Japan

[21] Appl. No.: 169,639

[22] Filed: Dec. 20, 1993

[30] Foreign Application Priority Data

Apr. 30, 1993 [JP] Japan .................................. 5-128102
Apr. 30, 1993 [JP] Japan .................................. 5-128103

[51] Int. Cl.$^5$ .................... C07C 45/50; B01J 23/40; B01J 20/26
[52] U.S. Cl. ............................. 562/519; 562/522; 562/607; 502/326; 502/402; 502/439; 502/507
[58] Field of Search ................... 562/519, 522, 607; 502/326, 402, 439, 507

[56] References Cited

U.S. PATENT DOCUMENTS

| | | |
|---|---|---|
| 3,769,329 | 10/1973 | Paulik et al. .................. 560/232 |
| 4,328,125 | 5/1982 | Drago et al. ................. 562/519 X |
| 5,155,261 | 10/1992 | Marston et al. ................ 562/519 |

Primary Examiner—Arthur C. Prescott
Attorney, Agent, or Firm—Lorusso & Loud

[57] ABSTRACT

A methanol carbonylation catalyst includes a rhodium complex supported on a porous, cross-linked vinylpyridine resin, wherein the vinylpyridine resin has a cross-linking degree of 30–60%, a pore volume of 0.1–0.4 ml/g and an average pore diameter of 20–100 nm. The catalyst may be prepared by contacting the pyridine ring-containing resin with an aqueous solution containing rhodium ion and then contacting the resulting rhodium ion-carrying resin with carbon monoxide and an alkyl iodide in an organic solvent to convert the rhodium ion to a rhodium complex bound to the resin. Acetic acid is produced by reacting carbon monoxide with methanol at a temperature of 140°–250° C. and a partial pressure of carbon monoxide of 7–30 kg/cm$^2$ in the presence of an alkyl iodide and the above catalyst.

11 Claims, 2 Drawing Sheets

SUPPORTED RHODIUM CATALYST, METHOD OF PREPARING SAME AND PROCESS OF PRODUCING ACETIC ACID BY METHANOL CARBONYLATION USING SAME

BACKGROUND OF THE INVENTION

This invention relates to a supported rhodium catalyst and a method of preparing same. The present invention is also directed to a process for the production of acetic acid from methanol and carbon monoxide using a supported rhodium catalyst.

U.S. Pat. No. 5,155,261 discloses a process for producing acetic acid by reacting methanol in a solvent with carbon monoxide in the presence of an alkyl iodide and a solid catalyst containing a rhodium complex supported on a porous, cross-linked vinyl pyridine resin carrier and suggests the preferability of using Reilex-425 (product of Reilly Tar and chemical Corporation) as the vinyl pyridine resin. The vinyl pyridine resin has a degree of cross-linking of 33% and a pore volume of 0.71 cc/g. The catalyst disclosed in this prior art has a satisfactory carbonylation activity.

However, it has now been found that the catalyst is ill-suited for the industrial production of acetic acid because of poor resistance to abrasion and resistance to elimination of pyridine rings thereof. Namely, the vinyl pyridine resin is not only gradually chemically decomposed but also gradually abraded or pulverized as the carbonylation is continued for a long period of time. The elimination of the pyridine rings makes it impossible to keep the catalytic activity constant and causes reduction of the catalyst life. The pulverization of the catalyst not only causes the reduction of the catalyst life but also requires the separation of the pulverized powder from the carbonylation reaction product.

Hitherto, supported rhodium catalyst has been prepared by contacting a pyridine-containing polymer with an organic solvent solution containing an alkyl iodide and a rhodium salt under a pressure of carbon monoxide. Since the solubility of a rhodium salt, such as $RhI_3$, in an organic solvent is very low, the rhodium salt is apt to be precipitated during the preparation of the catalyst. Thus, when the catalyst thus produced is separated from the reaction mixture, part of the precipitated rhodium salt is unavoidably admixed into the catalyst. This causes loss of very expensive rhodium. Further, another part of the precipitated rhodium deposits onto the inside wall of the reactor, which also causes loss of rhodium. The precipitation of the rhodium salt could be prevented by use of a large amount of the organic solvent. However, this is disadvantageous from the standpoint of economy not only because the additional cost of the organic solvent but also because the necessity of use of a large reactor.

SUMMARY OF THE INVENTION

It is, therefore, an object of the present invention to provide a stable catalyst having a high carbonylation activity, an excellent abrasion resistance and a long catalyst life.

Another object of the present invention is to provide a method which can produce a supported rhodium catalyst in an economical manner.

It is a further object of the present invention to provide a process which can produce acetic acid with a high yield in a stable manner.

In accomplishing the foregoing objects, the present invention provides a catalyst for the production of acetic acid from methanol and carbon monoxide, comprising a rhodium complex supported on a porous, cross-linked vinylpyridine resin, wherein said vinylpyridine resin has a cross-linking degree of 30–60%, a pore volume of 0.2–0.4 cc/g and an average pore diameter of 20–100 nm.

In another aspect, the present invention provides a method of preparing a supported rhodium catalyst, comprising the steps of:
(a) contacting a solid, pyridine ring-containing resin with an aqueous solution containing rhodium ion so that the rhodium ion is bound to said resin; and
(b) contacting said rhodium ion-carrying resin with carbon monoxide and an alkyl iodide in an organic solvent so that said rhodium ion is converted to a rhodium complex bound to said resin.

The present invention also provides a process for the production of acetic acid, comprising reacting carbon monoxide with methanol at a temperature of 140°–250° C. and a partial pressure of carbon monoxide of 7–30 $kg/cm^2$ in the presence of an alkyl iodide and the above catalyst.

BRIEF DESCRIPTION OF THE DRAWINGS

Other objects, features and advantages of the present invention will become apparent from the following description of the preferred embodiments of the invention which follows, when considered in light of the accompanying drawings, in which.

DETAILED DESCRIPTION OF THE PREFERRED EMBODIMENTS OF THE INVENTION

Figure 1:
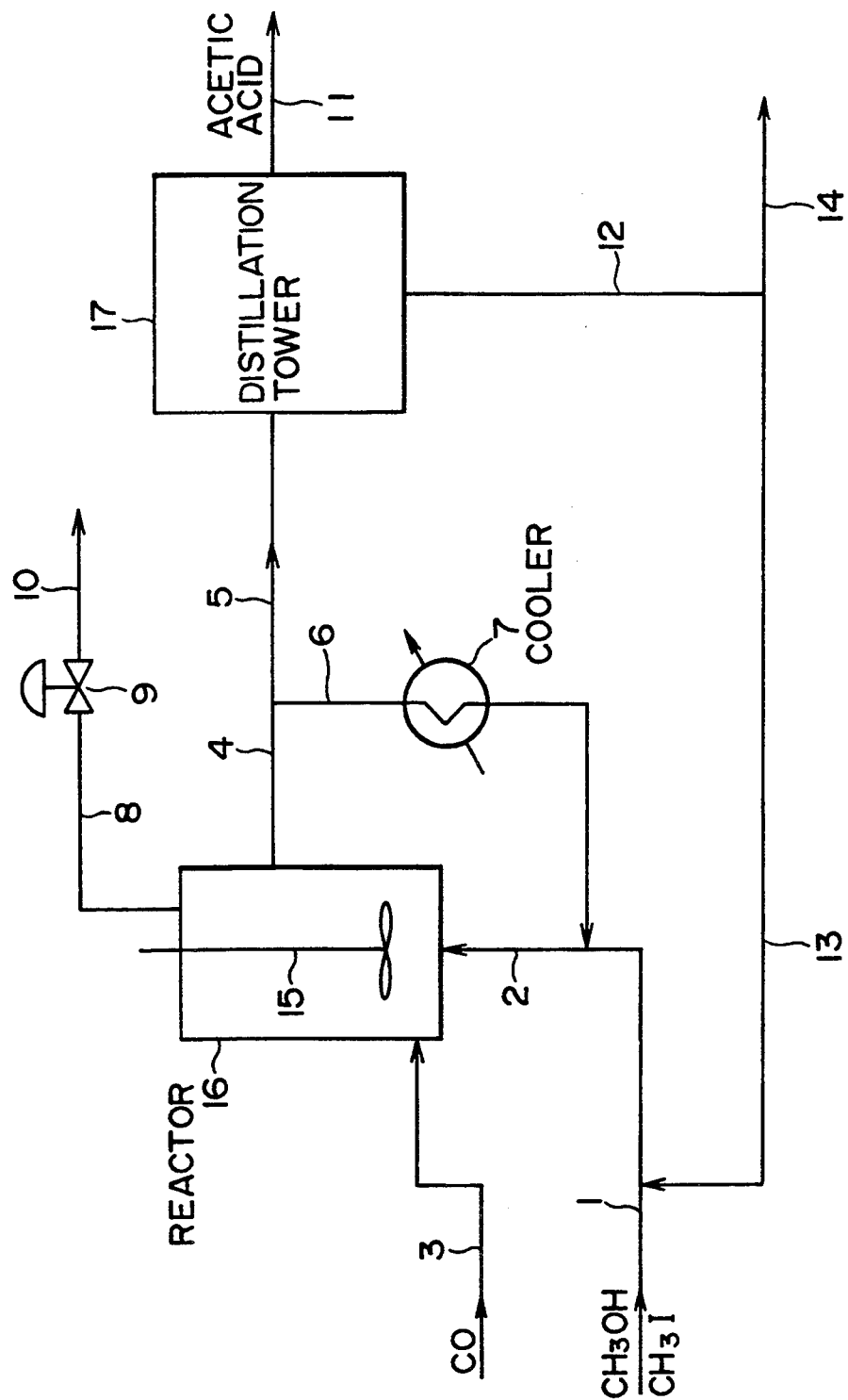
FIGS. 1 and 2 are flow diagrams each schematically illustrating an apparatus for carrying out the process of the present invention.

The novel catalyst comprises a rhodium complex supported on a porous, cross-linked vinylpyridine resin. It is important that the vinylpyridine resin have a cross-linking degree of 30–60%, preferably 35–60%, a pore volume of 0.2–0.4 cc/g, preferably 0.25–0.4 cc/g, and an average pore diameter of 20–100 nm, preferably 30–90 nm. This catalyst has an improved catalyst life and exhibits high mechanical strengths (e.g. resistance to abrasion and crushing) and high catalytic activity.

When the cross-linking degree of the cross-linked vinylpyridine resin (hereinafter referred to as VP resin for brevity) is less than 30%, the pyridine is apt to be eliminated from the catalyst during use and the abrasion resistance of the catalyst is lowered. Too high a cross-linking degree in excess of 60% is disadvantageous because the catalyst activity is lowered. A pore volume of at least 0.2 cc/g is required for obtaining a desired catalytic activity. When the pore volume exceeds 0.4 cc/g, lowering of the abrasion resistance results. An average pore diameter less than 20 nm causes reduction of the catalytic activity, while an average pore diameter in excess of 100 nm causes the reduction of abrasion resistance.

The term "cross-linking degree" herein is defined as follows:

Cross-linking degree (%)=$(A/B) \times 100$ wherein A represents the weight of the cross-linking agent contained in the VP resin and B represents the weight of the vinylpyridine monomer units of the VP resin.

The "pore volume" of the VP resin is measured by the mercury penetration method using Mercury Pressure Porosimeter Model 70 (manufactured by Carlo Elba Inc., Italy) with a mercury surface tension of 474 dyne/cm at 25° C., a contact angle of 140 degrees and an absolute mercury pressure varying from 1 to 200 kg/cm².

The term "average pore diameter" used herein is defined as follows:

Average pore volume (nm)=4(C/D)×10³ wherein C represents the pore volume (cc/g) of the VP resin and D represents the surface area (m²/g) of the VP resin measured by the B.E.T. method.

The VP resin may be produced by copolymerizing a vinylpyridine monomer with an aromatic compound having two vinyl groups as a cross-linking agent. The copolymerization method is well known in the art and may be, for example, a method in which a precipitant is added, a method in which a linear polymer is added, a method in which a swelling agent and a precipitant are added, and a method in which a diluent and a linear polymer are added. The method disclosed in Japanese Published Examined Patent Application No. 61-25731 may be particularly suitably used. In this method, a mixture containing a vinyl pyridine monomer, a cross-linking agent having two vinyl groups and, optionally, a vinyl monomer is reacted in the presence of a radical polymerization catalyst, a suspension stabilizing agent and a precipitant using an aqueous suspension polymerization technique. The stabilizer may be a water-soluble polymer such as polyvinyl alcohol, hydroxyethyl cellulose, carboxymethyl cellulose, sodium polymethacrylate, sodium polyacrylate, starch, gelatin, or an ammonium salt of styrene/meleic anhydride copolymer, or an inorganic salt such as calcium carbonate, calcium sulfate, bentonite or magnesium silicate. The precipitant is an organic liquid which serves to function as a good solvent for the monomer but as a poor solvent for the copolymer produced. Examples of the precipitant includes hydrocarbons having 5-10 carbon atoms such as isooctane, alcohols and esters. The polymerization degree of the VP resin may be controlled by control of the amount of the cross-linking agent. The pore volume and the average pore diameter may be controlled by selection of the kind and amount of the precipitant. Suitable selection of the kind and amount of the suspension stabilizer and the reaction temperature is also effective to control the pore characteristics of the VP resin.

Illustrative of suitable vinylpyridine monomers for the production of the VP resin are 4-vinylpyridine, 2-vinylpyridine and 2- and 4-vinylpyridine derivatives having a lower alkyl group such as a methyl group or ethyl group on the pyridine ring. The vinylpyridine monomer may be used in conjunction with an aromatic vinyl monomer such as styrene or vinyltoluene. Such a vinyl monomer is used in an amount of 30 mole % or less, preferably 20 mole % or less based on the total mole of total monomers. Illustrative of suitable cross-linking agents are aromatic divinyl compounds such as divinylbenzene and divinyltoluene and aliphatic divinyl compounds such as butadiene. The amount of the cross-linking agent is determined according to the intended cross-linking degree.

The VP resin is generally used in the form of beads, preferably spheres, having a particle size of 0.01-4 mm, preferably 0.1-2 mm, more preferably 0.4-2 mm. The VP resin is loaded with a rhodium complex [Rh(CO)₂I₂]⁻ in any suitable manner. The amount of the rhodium complex loaded on the VP resin is 0.2-2% by weight, preferably 0.5-1.0% by weight, in terms of elemental rhodium, based on the weight of the VP resin.

The loading of the VP resin with the rhodium complex may be performed by contacting the VP resin with a rhodium salt in a solvent containing an alkyl iodide under a pressure of carbon monoxide. This method may be carried out by contacting the rhodium salt with the VP resin under conditions as generally adopted in the catalytic carbonylation of methanol. During the course of the above reaction, the pyridine ring of the VP resin are quaternized with the alkyl iodide to form a pyridinium salt to which is ionically bonded a rhodium carbonyl complex [Rh(CO)₂I₂]⁻ formed by reaction of the rhodium salt, alkyl iodide and carbon monoxide.

Examples of the rhodium salts include rhodium halides such as rhodium chloride, rhodium bromide and rhodium iodide. Illustrative of suitable alkyl iodides are lower alkyl iodides such as methyl iodide, ethyl iodide and propyl iodide. The use of methyl iodide is preferred. The alkyl iodide is used in an amount of 2-2,000 moles, preferably 5-500 moles, per mole of the rhodium salt. The carbon monoxide pressure under which the rhodium salt is contacted with the VP resin in the presence of the alkyl iodide is 7-30 kg/cm²G, preferably 10-20 kg/cm²G.

The loading of the VP resin with the rhodium complex is preferably performed by a novel method which includes the steps of:
(a) contacting a solid, pyridine ring-containing resin with an aqueous solution containing rhodium ion so that the rhodium ion is bound to the resin; and
(b) contacting said rhodium ion-carrying resin with carbon monoxide and an alkyl iodide in an organic solvent so that the rhodium ion is converted to a rhodium complex bound to the resin. This method is also applicable to the production of conventional supported rhodium catalysts. Thus, any known VP resin can be also loaded with the rhodium complex using the novel method.

In the novel method, the VP resin is first contacted with an aqueous solution containing rhodium ions so that the rhodium ions are bound to pyridine rings of the resin:

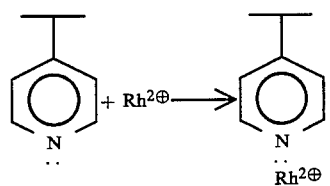

The aqueous solution may be prepared by dissolving a water soluble rhodium salt such as rhodium chloride, rhodium bromide or rhodium iodide and preferably has a rhodium concentration of 1,000-5,000 ppm by weight, more preferably 1,500-4,000 ppm by weight, in terms of elemental rhodium. The contact of the resin with the aqueous solution may be performed, for example, by immersing the resin in the solution or by passing the solution through a column packed with the resin at a temperature of generally 20°-70° C., preferably 25°-50°

C., for a period of time so that desirably 0.2–2% by weight of rhodium ions in terms of elemental rhodium is bound to the resin.

The resin to which rhodium ions have been bound is then contacted with an alkyl iodide and carbon monoxide in an organic solvent so that the rhodium ion bound to the pyridine ring is converted into rhodium complex bound to the pyridinium nitrogen quaternized by reaction with the alkyl iodide:

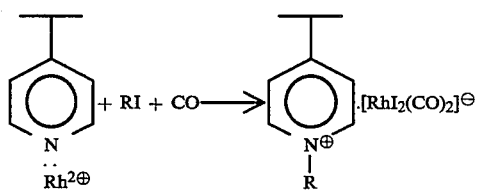

The alkyl iodide, which is preferably methyl iodide, is used in an amount of generally 2–2,000 moles, preferably 50–500 moles, per mole of the rhodium ions bound to the resin. As the organic solvent, there may be used alcohols such as methanol, ethanol and propanol, carboxylic acids such as acetic acid and propionic acid, esters such as methyl acetate, ethyl acetate and methyl propionate, and dialkyl ethers such as dimethyl ether. The organic solvent may contain up to 10% by weight of water. The amount of the rhodium ion-carrying resin is generally 2–25% by weight, preferably 5–10% by weight based on the weight of the organic solvent. The above reaction is generally performed at a temperature of 140°–250° C., preferably 160°–200° C. under a partial pressure of carbon monoxide of generally 5–30 kg/cm$^2$, preferably 10–25 kg/cm$^2$. The thus obtained rhodium complex loaded resin may be used as such for carbonylation of an alcohol but, if desired, may be separated from the reaction solvent and washed with an organic solvent such as methanol or acetic acid.

In the above method, the VP resin is first contacted with an aqueous solution containing rhodium cation to capture the rhodium cation. Since a rhodium salt is highly soluble in water, no rhodium salt precipitates throughout this first step. The aqueous solution after contact with the VP resin which still contains unbound rhodium cation can be reused after being added with a supplemental amount of the rhodium salt for adjusting the rhodium concentration. Therefor, all of the rhodium salt can be effectively utilized without loss. In the second step, the rhodium ion-carrying VP resin is reacted with an alkyl iodide and carbon monoxide in an organic solvent. Since the rhodium ion is ionically bound to the pyridine ring of the VP resin, no precipitates of rhodium salt are formed in the organic solvent during the course of the second step.

The thus prepared catalyst is advantageously used for the carbonylation of a lower alcohol, especially methanol. Acetic acid is produced by a process which comprises reacting carbon monoxide with methanol under a carbon monoxide pressure in the presence of an alkyl iodide and the above catalyst.

The carbonylation of methanol using the above heterogeneous catalyst may be carried out using any desired reactor, such as a fixed bed reactor, an expansion bed reactor or a stirred tank reactor. The catalyst is placed in the reactor in an amount of, generally, 2–40% by weight based on the weight of the reaction solution contained therein, though the amount varies with the kind of the reactor used. It is recommendable to use the catalyst in an amount of 2–25% by weight in the case of a mixing type reactor, 20–40% by weight in the case of a fixed bed reactor and 2–25% by weight in the case of an expansion bed reactor, based on the reaction solution contained therein.

As the reaction solvent, a carbonyl group-containing compound having at least two carbon atoms is suitably used. Such a compound may be, for example, a saturated aliphatic acid such as acetic acid, propionic acid or butyric acid, an ester such as methyl acetate or ethyl acetate, an aromatic acid such as benzoic acid, or a mixture thereof. The solvent can contain up to 50% by weight, preferably 0.1–20% by weight of water. The alkyl iodide is preferably a lower alkyl iodide having 1–6 carbon atoms, such as methyl iodide.

It is preferred that the reaction solution within the reactor have a content of the carbonyl group-containing solvent of at least 0.30 part by weight per part by weight of the methanol present in the reaction solution within the reactor. By using such an organic solvent in such a specific amount, the catalyst can exhibit high catalytic activity and the dissociation of rhodium species from the polymer substrate can be minimized, so that the reaction can be performed at a low carbon monoxide partial pressure. Especially good results are obtainable with the use of the organic solvent in an amount of at least 2.4 parts by weight per part by weight of the methanol.

The term "the reaction solution within the reactor" used herein is intended to mean the solution which is present in the reactor at any point in time in the course of the reaction. Since methanol is consumed as the reaction proceeds, the relative amount of the solvent increases as the reaction proceeds. Thus, in the case of a batch type reactor, for example, the solution may be the raw material feed introduced into the reactor. In the case of a continuous flow, stirred tank-type reactor, the solution may be the product continuously discharged from the reactor. In the case of a piston flow type reactor, the solution may be the whole feed, inclusive of recycled solutions, to the reactor.

The methanol carbonylation is performed at a temperature of 140°–250° C., preferably 160°–200° C. and a carbon monoxide partial pressure of 7–30 kg/cm$^2$, preferably 10–20 kg/cm$^2$, while maintaining the total reaction pressure in the range of 15–60 kg/cm$^2$G, preferably 15–40 kg/cm$^2$G, more preferably 15–30 kg/cm$^2$G. The alkyl iodide, which is preferably methyl iodide, is used in an amount effective to promote the methanol carbonylation, generally in an amount of 1–40% by weight, preferably 5–30% by weight, based on the weight of the solution within the reactor. The rhodium loaded catalyst is used in a catalytically effective amount, generally in an amount of at least 50 ppm by weight, preferably at least 300 ppm by weight, more preferably at least 400 ppm by weight, in terms of elemental rhodium, based on the weight of the solution within the reactor.

Referring to FIG. 1, designated as 16 is a reactor containing a rhodium-loaded catalyst, acetic acid as a solvent and methyl iodide as a promoter. The contents in the reactor 16 are homogeneously mixed with a stirrer 15. To the reactor 16 is continuously fed methanol containing methyl iodide through lines 1 and 2 and, at the sane time, carbon monoxide gas is continuously introduced into the reactor 16 through a line 3. The methanol and carbon monoxide are contacted with the catalyst in the reactor 16 to produce acetic acid.

The product solution is continuously discharged from the reactor 16 through a line 4 and a portion thereof is fed, through a line 6, to a cooler 7 where it is cooled by indirect heat exchange with a cooling medium with the other portion thereof being fed to a distillation tower 17 through a line 5. The solution cooled in the cooler 7 is recycled to the reactor 16 to maintain the temperature of the reaction solution within the reactor 16 at a predetermined range. The product solution introduced into the distillation tower 17 is separated into acetic acid which is recovered through a line 11 and a residual liquid. Part of the residual liquid containing by products, such as water, hydrogen iodide, methyl acetate and dimethyl ether, as well as unreacted methanol, methyl iodide and, if desired, acetic acid is recycled through lines 12, 13 and 2 to the reactor 16 while the other part thereof is, if necessary, discharged from the reaction system through a line 14.

A gas containing unreacted carbon monoxide and vapors of low boiling point matters such as methyl iodide is withdrawn overhead from the reactor 16 and is passed through a line 8, a flow control valve 9 and a line 10 to a suitable separating device (not shown) to separate the low boiling point matters which may be recycled to the reactor 16, if desired. In lieu of the mechanical stirrer 15, the stirring of the reaction solution may be effected by any suitable method such as by introducing the feed gas and/or liquid as a jet stream. The cooling of the product solution for controlling the reaction solution may be effected by any other suitable means such as by flushing.

Figure 2:
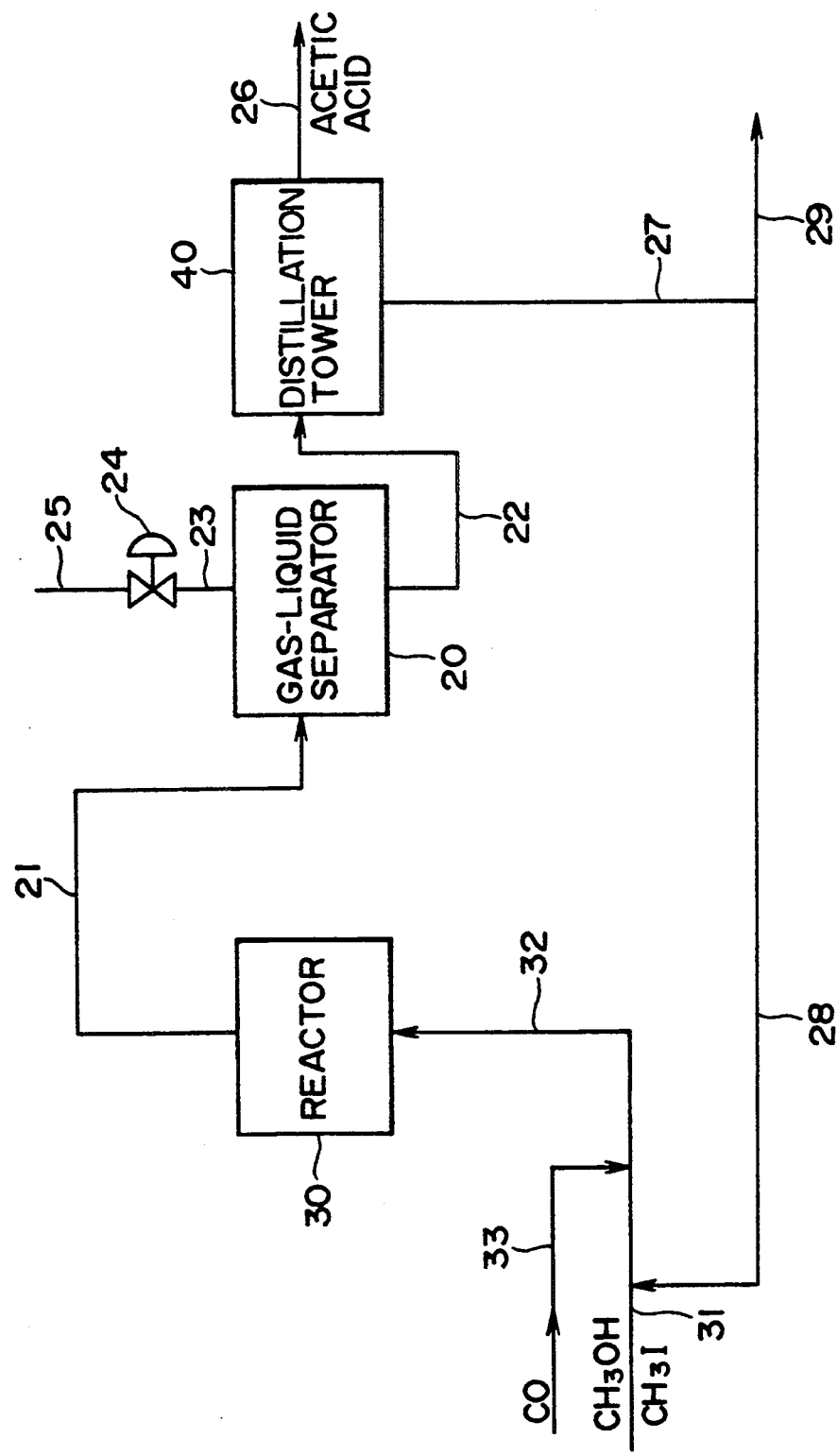

FIG. 2 illustrate a methanol carbonylation system using a piston flow-type reactor 30. The reactor 30 has a plurality of pipes (not shown) connected in parallel with each other and each packed with a rhodium-loaded catalyst. The packed catalyst may be in the form of a fixed bed or an expansible bed. The pipes are surrounded by a sheath into which a cooling medium such as low temperature steam is supplied for indirect heat exchange with the reaction solution flowing within the pipes. The heated steam be used, for example, as a heat source for a distillation tower 40.

Raw material methanol and methyl iodide are supplied through a line 31 and is introduced, together with carbon monoxide supplied through a line 33 and a solvent-containing recycled solution supplied through a line 28, into an inlet port of the reactor 30 through a line 32, where the liquid/gas feeds are thoroughly mixed with each other. The mixture is then evenly introduced into respective catalyst-containing pipes and is reacted to produce acetic acid.

The reaction mixture is withdrawn from the top of the reactor 30 and is fed to a gas-liquid separator 20 through a line 21, where it is separated into a gas containing unreacted carbon monoxide and a liquid product containing acetic acid. The gas is discharged from the separator 20 and is passed through a line 23, a flow control valve 24 and a line 25 to a suitable separating device (not shown) to separate the low boiling point matters which may be recycled to the reactor 30, if desired. The liquid product separated from the gas is fed through a line 22 to a distillation tower 40 where it is separated into acetic acid which is recovered through a line 26 and a residual liquid which is discharged from the tower 40 though a line 27. A portion of the residual liquid containing by-products, such as water, hydrogen iodide, methyl acetate and dimethyl ether, as well as unreacted methanol, methyl iodide and, if desired, acetic acid is recycled through lines 28 and 32 to the reactor 30 while the other portion thereof is, if necessary, discharged from the reaction system through a line 29.

The following examples will further illustrate the present invention. Percentages, parts and ppm are by weight except otherwise noted.

EXAMPLE 1

Preparation of VP Resins

VP Resin-A

77 Parts by weight of vinylpyridine and 38 parts by weight of divinylbenzene (containing 40% by weight of ethylvinylbenzene) were copolymerized using isooctane as a precipitant to obtain VP Resin-A having an average particle size of 0.5 mm.

VP Resin-B

72 Parts by weight of vinylpyridine and 47 parts by weight of divinylbenzene (containing 40% by weight of ethylvinylbenzene) were copolymerized using isooctane as a precipitant to obtain VP Resin-B having an average particle size of 0.5 mm.

VP Resin-C

67 Parts by weight of vinylpyridine and 56 parts by weight of divinylbenzene (containing 40% by weight of ethylvinylbenzene) were copolymerized using isooctane as a precipitant to obtain VP Resin-C having an average particle size of 0.6 mm.

VP Resin-D

63 Parts by weight of vinylpyridine and 63 parts by weight of divinylbenzene (containing 40% by weight of ethylvinylbenzene) were copolymerized using isooctane as a precipitant to obtain VP Resin-D having an average particle size of 0.7 mm.

VP Resin-E

77 Parts by weight of vinylpyridine and 67 parts by weight of divinylbenzene (containing 40% by weight of ethylvinylbenzene) were copolymerized using isooctane as a precipitant to obtain VP Resin-E having an average particle size of 0.65 mm.

Physical Properties of VP Resins

The cross-linking degree, pore volume, surface area and average pore diameter of the thus obtained VP resins were measured and are shown in Table 3 together with those of commercially available VP resins Reillex 402 (manufactured by Reilly Tar and Chemical Company; average particle size: below 0.2 mm (powder)), Reillex 425 (manufactured by Reilly Tar and Chemical Company; average particle size: 0.55), KEX 316 (manufactured by Koei Chemical Company; average particle size: 0.65 mm) and KEX 212 (manufactured by Koei Chemical Company; average particle size: 0.1 mm).

Abrasion Resistance of VP Resins

Into a one-liter glass vessel were charged 500 g of acetic acid and 25 g (on dry basis) of the above-mentioned VP resin. The contents were stirred with a stirrer having a stainless steel blade (3.2 cm × 1.2 cm) at a rotational speed of 1,000 rpm for 1,000 hours. Fine particles having a particle size of about 10 μm or less were then separated, dried and measured for the weight W from which the powder-forming rate $R_1$ is calculated as follows:

$$R_1 = W/25 \times (100/1,000)(\%/\text{hour})$$

The results are summarized in Table 1.

Pyridine-Elimination Resistance of VP Resins

The above-mentioned VP resin (10 g) was treated with 90 ml of a 90% aqueous acetic acid solution at 110° C. under reflux for 140 hours. The solution was then analyzed for determining the nitrogen content. The pyridine elimination rate $R_2$ is calculated as follows:

$$R_2 = 100N/14N_0 (\%/\text{hour})$$

wherein N is the concentration (% by weight) of nitrogen contained in the solution and $N_0$ is the content (% by weight) of nitrogen in the VP resin. The results are shown in Table 1.

Preparation of Supported Rhodium Catalysts and Evaluation of Catalytic Activities Thereof:

lation degree (mol/mol) of the starting material, Mc represents concentration of methyl groups (mol/liter) in the reaction solution and H represents the reaction time (hour). Carbonylation degree Cr is defined as follows:

$$Cr = \frac{\text{Concentration of methyl groups carbonylated (mol/liter)}}{\text{Concentration of total methyl groups (mol/liter)}}$$
$$= (M[CH_3COOH] + M[CH_3COOCH_3])/$$
$$(M[CH_3COOH] + 2M[CH_3COOCH_3] + 2M[CH_3OCH_3] + M[CH_3OH])$$

wherein $M[CH_3COOH]$, $M[CH_3COOCH_3]$, $M[CH_3OCH_3]$ and $M[CH_3OH]$ represent the amounts, in terms of molarity, of $CH_3COOH$, $CH_3COOCH_3$, $CH_3OCH_3$ and $CH_3OH$, respectively which are present in the solution within the reactor. The results are shown in Table 1 below.

TABLE 1

| VP Resin | Cross-linking Degree (%) | Pore Volume (cc/g) | Surface Area (m²/g) | Average Pore Diameter (nm) | Powder Forming Rate $R_1$ (%/hour) | Pyridine Elimination Rate $R_2$ (%/hour) | Carbonylation Rate STY (mole/liter hour) |
|---|---|---|---|---|---|---|---|
| Reillex 402* | 4 | — | — | 0 | ** | $1.2 \times 10^{-2}$ | 0 |
| Reillex 425* | 29 | 0.710 | 33.0 | 86.1 | $4.4 \times 10^{-3}$ | $5.6 \times 10^{-3}$ | 3.87 |
| KEX 316* | 11 | 0.219 | 5.1 | 171.8 | $2.0 \times 10^{-3}$ | $2.7 \times 10^{-2}$ | 4.50 |
| KEX 212* | 23 | 0.143 | 13.0 | 44.0 | $9.6 \times 10^{-4}$ | $3.1 \times 10^{-3}$ | 2.92 |
| VP Resin-A | 30 | 0.212 | 18.0 | 47.1 | $8.2 \times 10^{-4}$ | $6.2 \times 10^{-4}$ | 3.88 |
| VP Resin-B | 39 | 0.317 | 15.7 | 80.8 | $4.0 \times 10^{-5}$ | $7.1 \times 10^{-4}$ | 4.26 |
| VP Resin-C | 50 | 0.325 | 24.2 | 53.7 | $2.5 \times 10^{-5}$ | $3.4 \times 10^{-4}$ | 3.32 |
| VP Resin-D | 60 | 0.267 | 32.0 | 33.4 | $2.7 \times 10^{-5}$ | $7.1 \times 10^{-5}$ | 3.30 |
| VP Resin-E* | 68 | 0.215 | 35.5 | 24.2 | $1.7 \times 10^{-5}$ | $3.3 \times 10^{-5}$ | 1.56 |

*: Comparative Sample
**: Unable to measure because the sample is fine powder

Using the VP resins shown in Table 1, supported rhodium catalysts were prepared. Thus, 6.7 g (on dry basis) of each resin was charged in a 250 ml autoclave, equipped with a stirring blade, together with a mixed liquid consisting of 0.15 g of rhodium chloride trihydrate, 62.3 g of methanol, 65.2 g of acetic acid and 11.1 g of methyl iodide. After deaeration with carbon monoxide gas, the autoclave was heated to 190° C. Then, with stirring at 600 rpm, carbon monoxide was charged thereinto until a total pressure of 50 kg/cm² resulted. The temperature within the autoclave was maintained at 190° C. for 30 minutes while maintaining the pressure therewithin at 50 kg/cm² with a pressure control valve. Then the autoclave was cooled to room temperature and was purged with nitrogen gas. The supernatant was removed by decantation and the solids were washed several times with methanol to obtain a rhodium-loaded resin catalyst.

The catalyst thus obtained was placed in the same autoclave, to which a mixed liquid consisting of 65.2 g of acetic acid, 62.3 g of methanol and 11.1 g of methyl iodide was charged. After the autoclave had been heated to 190° C., carbon monoxide was charged thereinto until a total pressure of 50 kg/cm² resulted. The contents in the autoclave were reacted at that temperature for 1 hour with stirring at 600 rpm. The reaction mixture was then analyzed to determine the amount of carbon monoxide reacted, from which the carbonylation rate in terms of space time yield STY was calculated according to the following equation.

$$STY = (Cr - Cf) \times Mc/H$$
$$= (Cr - 0.36) \times 22/1 \text{ (mole/liter hour)}$$

wherein Cr represents the carbonylation degree (mol/mol) of the reaction solution, Cf represents the carbony-

EXAMPLE 2

The VP Resin-B obtained in Example 1 was loaded with various amounts of the rhodium complex in the same manner as described in Example 1 to obtain Catalysts Nos. 1-5. Each of the thus obtained Catalysts Nos. 1-5 was tested for the space time yield STY in the same manner as that in Example 1 to give the results shown in Table 2. From STY, the reaction rate per mole of rhodium was calculated. Further, the concentration of the rhodium liberated from the catalyst and contained in the reaction solution was measured. The results are also summarized in Table 2.

TABLE 2

| Catalyst No. | Amount of Supported Rhodium (wt. %)** | STY (mol/liter · hr) | Reaction Rate per mole of Rhodium (mol/molRh · sec) | Concentration of Rhodium in Reaction Solution (ppm) |
|---|---|---|---|---|
| 1 | 9.2 | 8.1 | 3.1 | 12.03 |
| 2 | 5.2 | 7.5 | 5.1 | 5.23 |
| 3 | 2.0 | 6.2 | 11.1 | 2.12 |
| 4* | 0.8 | 4.3 | 19.2 | 0.77 |
| 5 | 0.2 | 3.2 | 57.2 | 0.08 |

*The same catalyst as obtained in Example 1
**Based on the weight of the resin

EXAMPLE 3

Using various amounts of the Catalysts No. 2 and No. 4 obtained in Example 2, tests were performed for STY and the concentration of rhodium liberated from the catalyst into the reaction solution in the same manner as that in Example 2. The results are summarized in Table 3. The amount of the catalyst is expressed in terms of % based on the raw material feed charged in the autoclave.

TABLE 3

| Catalyst No. | Amount of Catalyst (%) | STY (mol/liter · hr) | Concentration of Rhodium in Reaction Solution (ppm) |
| --- | --- | --- | --- |
| 2 | 7 | 7.5 | 5.0 |
| 2 | 10 | 10.5 | 5.1 |
| 2 | 15 | 15.9 | 5.2 |
| 4 | 7 | 4.3 | 0.8 |
| 4 | 10 | 6.0 | 0.8 |
| 4 | 15 | 9.1 | 0.8 |

From the results shown in Tables 2 and 3, it will be appreciated that the amount of the rhodium species liberated from the catalyst depends on the amount of the rhodium supported on the VP resin but is independent from the amount of the catalyst used.

EXAMPLE 4

Using a reaction apparatus as illustrated in FIG. 1, methanol carbonylation was continuously performed. The catalytic activity after 4,000 hours process time was substantially the same as that in the initial stage. The operation conditions were as follows:

Line 2

| Composition: | |
| --- | --- |
| Methanol | 40% |
| Methyl Iodide | 10% |

Flow Rate: 200 parts per hour
Line 3

| Composition: | |
| --- | --- |
| Carbon Monoxide | 100 mol % |

Flow Rate: 16 parts per hour

| Reaction Conditions | |
| --- | --- |
| Temperature | 190° C. |
| CO Pressure | 15 kg/cm$^2$ |
| Total Pressure | 45 kg/cm$^2$ |
| Catalyst | No. 4 of Example 2 |
| Amount of Catalyst | 10% based on the reactant in reactor |
| Rhodium Concentration | 800 ppm based on the reactant in reactor |
| Stirring Speed | 300 rpm |

Line 4

| Composition: | |
| --- | --- |
| Methanol | 0.5% |
| Acetic Acid | 65% |
| Methyl Iodide | 10% |
| Others | 24.5% |

Flow Rate: 225 parts/hour

EXAMPLE 5

Preparation of Supported Rhodium Catalyst by Novel Method:

The VP Resin-B obtained in Example 1 was mixed with 196 ml of an aqueous solution containing 4,350 ppm of rhodium chloride (1,700 ppm as rhodium ion) and the mixture was gently stirred at room temperature for 18 hours. The atomic absorption analysis revealed that the concentration of rhodium ion in the resulting aqueous solution was decreased to 1,200 ppm. Thus, the vinylpyridine resin was found to bind rhodium ions in an amount of 14.6 mg in terms of elemental rhodium per one gram of the resin. The rhodium ion-carrying resin was then charged in a 250 ml autoclave, equipped with a stirring blade, together with 140 g of a solution containing 8% of methyl iodide, 40% of methanol and 52% of acetic acid. After deaeration with carbon monoxide gas, the mixture was heated to 190° C. with stirring at 600 rpm. Then, carbon monoxide was fed to the autoclave through a pressure control valve so that the pressure within the autoclave showed about 40 kg/cm$^2$G (initial partial pressure of carbon monoxide: 15 kg/cm$^2$). The mixture within the autoclave was reacted at those temperature and pressure for 1 hour. Then the autoclave was cooled to room temperature and was purged with nitrogen gas. The supernatant was removed by decantation and the solids were washed several times with methanol to obtain a rhodium-loaded resin catalyst. Since substantially no Rh was contained in the supernatant, the amount of Rh loaded on the resin is considered to be 14.6 mg per one gram resin. This catalyst was found to exhibit excellent methanol carbonylation activity.

EXAMPLE 6

The VP Resin-B obtained in Example 1 was immersed in methanol for impregnation therewith. This was then charged in a 250 ml autoclave, equipped with a stirring blade, together with 0.3 g of RhCl$_3$.3H$_2$O and 140 g of a solution containing 8% of methyl iodide, 40% of methanol and 52% of acetic acid. After deaeration with carbon monoxide gas, the mixture was heated to 190° C. Then, carbon monoxide was fed to the autoclave through a pressure control valve so that the pressure within the autoclave showed about 40 kg/cm$^2$G (initial partial pressure of carbon monoxide: 15 kg/cm$^2$). The mixture within the autoclave was reacted at those temperature and pressure for 1 hour. Then the autoclave was cooled to room temperature and was purged with nitrogen gas. The supernatant was removed by decantation and the solids were washed several times with methanol to obtain a rhodium-loaded resin catalyst. The atomic absorption analysis revealed that the amount of Rh contained in the supernatant was 1430 ppm so that the amount of Rh loaded on the resin was 14.8 mg per one gram resin. Precipitates were observed in the supernatant.

EXAMPLE 7

Example 5 was repeated in the same manner as described except that VP Resin-E obtained in Example 1 was substituted for VP Resin-B, thereby obtaining a supported catalyst having rhodium content of 13.7 mg per 1 g of the VP resin. Substantially no rhodium was detected in the supernatant.

EXAMPLE 8

Example 6 was repeated in the same manner as described except that VP Resin-E obtained in Example 1 was substituted for VP Resin-B, thereby obtaining a supported catalyst having rhodium content of 14.0 mg per 1 g of the VP resin. Precipitates were found to be formed in the supernatant.

EXAMPLE 9

Each of the catalysts obtained in Examples 5-8 was placed in a 250 ml autoclave, equipped with a stirring blade, together with 140 g of a solution containing 8% of methyl iodide, 40% of methanol and 52% of acetic acid. After deaeration with carbon monoxide gas, the mixture was heated to 190° C. Then, carbon monoxide was fed to the autoclave through a pressure control valve so that the pressure within the autoclave showed about 40 kg/cm$^2$G (initial CO partial pressure of 15 kg/cm$^2$). The contents in the autoclave were reacted at that temperature for 1.5 hour with stirring. The reaction mixture was then analyzed to determine the amount of carbon monoxide reacted, from which the carbonylation rate in terms of space time yield STY was calculated in the manner previously mentioned. The results are shown in Table 4.

TABLE 4

| Catalyst | Amount of Rhodium Loaded (%) | STY (mol/liter · hr) |
|---|---|---|
| Example 5 | 1.46 | 5.8 |
| Example 6 | 1.48 | 5.9 |
| Example 7 | 1.37 | 2.0 |
| Example 8 | 1.40 | 2.0 |

From the results shown in Table 4, it will be appreciated that the difference in the method of preparing the catalyst does not cause any difference in the catalytic activity.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

What is claimed is:

1. A catalyst for the production of acetic acid from methanol and carbon monoxide, comprising a rhodium complex supported on a porous, cross-linked vinylpyridine resin, wherein said vinylpyridine resin has a cross-linking degree of 30-60%, a pore volume of 0.2-0.4 cc/g and an average pore diameter of 20-100 nm.

2. A catalyst as claimed in claim 1, wherein said vinylpyridine resin is a copolymer of vinylpyridine and styrene.

3. A catalyst as claimed in to claim 1, wherein said vinylpyridine resin contains divinylbenzene as a cross-linking agent.

4. A catalyst as claimed in claim 1, wherein the amount of said rhodium complex is 0.2-2% by weight in terms of elemental rhodium based on the weight of said vinylpyridine resin.

5. A method of preparing a supported rhodium catalyst, comprising the steps of:
    (a) contacting a solid, pyridine ring-containing resin with an aqueous solution containing rhodium ion so that the rhodium ion is bound to said resin; and
    (b) contacting said rhodium ion-carrying resin with carbon monoxide and an alkyl iodide in an organic solvent so that said rhodium ion is converted to a rhodium complex bound to said resin.

6. A method as claimed in claim 5, wherein said organic solvent includes a mixture of methanol with acetic acid.

7. A method as claimed in claim 5, wherein step (a) is performed at a temperature of 20°-70° C.

8. A method as claimed in claim 5, wherein step (b) is performed at a temperature of 50°-250° C. under a carbon monoxide partial pressure of 5-30 kg/cm$^2$.

9. A method as claimed in claim 5, wherein said pyridine ring-containing resin has a cross-linking degree of 30-60%, a pore volume of 0.1-0.4 cc/g and an average pore diameter of 20-100 nm.

10. A catalyst obtained by a method according to claim 9.

11. A process for the production of acetic acid, comprising reacting carbon monoxide with methanol at a temperature of 140°-250° C. and a partial pressure of carbon monoxide of 7-30 kg/cm$^2$ in the presence of an alkyl iodide and a catalyst according to claim 1.

* * * * *